United States Patent [19]
Petruska et al.

[11] Patent Number: 5,755,750
[45] Date of Patent: May 26, 1998

[54] METHOD AND APPARATUS FOR SELECTIVELY INHIBITING ACTIVITY IN NERVE FIBERS

[75] Inventors: Jeffery C. Petruska, Melrose; Richard D. Johnson, Gainesville, both of Fla.

[73] Assignee: University of Florida, Gainesville, Fla.

[21] Appl. No.: 746,355

[22] Filed: Nov. 8, 1996

Related U.S. Application Data

[60] Provisional application No. 60/006,457 Nov. 13, 1995.

[51] Int. Cl.$^6$ .................................................. A61N 1/18
[52] U.S. Cl. .................................................. 607/75; 607/118
[58] Field of Search ........................... 607/118, 75, 72, 607/73, 74, 46

[56] References Cited

U.S. PATENT DOCUMENTS 4,628,942  12/1986  Sweeney et al. .
5,199,430   4/1993  Fang et al. .

OTHER PUBLICATIONS

Small–Nerve Junctional Potentials, The Distribution of Small Motor Nerves to Frog Skeletal Muscle, and the Membrane Characteristics of the Fibres They Innervate. J. Physiol. (1953) 121, 289–317.

Presynaptic Hyperpolarization: A Role for Fine Afferent Fibres. J. Physiol (1964), 172, pp. 274–294 With 7 text-figures, printed in Great Britain.

Observations on Anodal Polarization of Cutaneous Nerve. Kenneth L. Casey and Marjorie Blick, Brain Research, 13 (1969) 155–167.

Differential Block of Conduction of Larger Fibers in Peripheral Nerve by Direct Current, M. Manfredi, Arch. Ibal. Biol. 108: 52–71 (1970).

Assessment of Differential Block of Conduction by Direct Current Applied to the Cervical Vagus Nerve, Diana Trenchard and J. G. Widdicombe, ACTA Neurobiol. Exp. 1973, 22:89–96.

Article: J. Physiol. (1972) 222: 66P–67P.
Article: J. Physiol. (1973) 232: 9P–10P.

(List continued on next page.)

*Primary Examiner*—Scott M. Getzow
*Attorney, Agent, or Firm*—Quarles & Brady

[57] ABSTRACT

Activity in different fibers of a nerve in an animal can be selectively blocked by applying direct electric current between an anode and a cathode attached to the nerve. The anode has base of silver foil with a tough shaped portion which has a first curved region coated with silver/silver chloride for contacting the nerve. The cathode includes a silver foil base which also has a tough shaped portion with a second curved region coated with silver/silver chloride for contacting the nerve. The second region is at least six times greater in area than the first region, so that the density of current conducted between the cathode and the nerve is significantly less than the current density at the anode. A signal generator produces a direct current stimulation signal between positive and negative output terminals that are connected respectively to the anode and cathode.

22 Claims, 11 Drawing Sheets

OTHER PUBLICATIONS

Differential Blocking of Motor Fibers by Direct Current, K. Fukushima, O. Yahara and M. Kato, Pflügers Arch. 358, 235–242 (1975).

Selective Activation of Peripheral Nerve Fibre Groups of Different Diameter by Triangular Shaped Stimulus Pulses, Neri Accornero, Giorgio Bini, Gian Luig Lenzi and Mario Manfredi, J. Physiol. (1977), 273 pp. 539–560, with 10 text–figures, Printed in Great Britain.

Anodal Block of Medullated Cardiopulmonary Vagal Afferents in Cats, Peter Thoren, John T. Shepherd and David E. Donald, (1977).

Effect of Anodal Blockade of Myelinated Fibers on Vagal C–Fiber Afferents, F. A. Hopp, E. J. Zuperku, R. L. Coon and J. P. Kampine, Amer. Physiol., (1980) 239: R454–462.

An Asymmetric Two Electrode Cuff for Generation of Unidirectionally Propagated Action Potentials, James D. Sweeney and J. Thomas Mortimer, IEEE Transactions on Biomedical Engineering, vol. BME–33, No. 6 Jun. 1986.

A Modified "Triangular Pulse" Stimulator for C–Fibers Stimulation, F. S. –Jaw., C. –T Yen, H.W. Tsao and H.J. Yu, Journal of Neuroscience Methods, 37 (1991) 169–172.

Alternate Excitation of Large and Small Axons With Different Stimulation Waveforms: An Application to Muscle Activation, Z.P. Fang, J.T. Mortimer, Medline—Med–Bio-1–Eng–Comput. 1991 Sep.; 29(5); 543–7.

METHOD AND APPARATUS FOR SELECTIVELY INHIBITING ACTIVITY IN NERVE FIBERS

This application claims benefit of U.S. Provisional Application Ser. No. 60/006,457, filed Nov. 13, 1995.

BACKGROUND OF THE INVENTION

The present invention relates to methods and apparatus to block nerve activity in animals, especially humans; and more particularly to the selective blocking of activity in specific types of fibers within the nerve while not affecting activity in other fibers.

Blocking of nerve activity has many clinical and research applications. For example, blocking of the correct axons in a nerve provides spinal cord injury patients with means to control urinary sphincter spasticity. Intractable hiccups also can be managed with nerve blocking.

In research applications the anodal block technology has already been used to further test the idea that different types of sensory information (i.e., touch, pain, etc.) are carried on different types of primary afferents and that these afferents transmit their information to different areas of the brain (Petruska, J. C., Hubscher, C. H., Johnson, R. D. "Anodally-Focussed Polarization Allows Differentiation of Large and Small Primary Afferent Input to Caudal Brainstem," *Soc. Neurosci. Abst.* 22:1, 1996). This idea of segregation of information has prevailed for many years. A prime example is the processing of light touch information from the body. It is known that the primary afferent central axons that carry light touch information travel in the dorsal columns of the spinal cord. The first central synapse in the light touch pathway is the dorsal column nuclei (DCN) of the brainstem. Until recently it was believed that the dorsal column nuclei received only myelinated fiber input, even though work had shown that unmyelinated axons also traveled in the dorsal columns. We have been testing whether or not the DCN receive input from unmyelinated primary afferent axons by utilizing the anodal block technology. By blocking the conduction in the myelinated axons, we have found that there are cells in the DCN that do receive input from these unmyelinated primary afferents. Most also received input from the faster myelinated fibers, and the response of the DCN neurons to input from the two types of afferents differed. Most cells that responded to unmyelinated fiber input had high threshold peripheral receptive fields in addition to their low threshold receptive fields. This information may lead to new understandings regarding the processing of information, especially as regards the segregation of information in central processing centers. Such understanding could have significant influences on how sensory abnormalities (eg., chronic pain syndromes) are treated clinically.

There are two different kinds of nerve fibers, myelinated and unmyelinated. The myelinated fibers are relatively large with a thick sheath for insulation, while unmyelinated nerve fibers are smaller and lack the insulating sheath. As the phylogenetically oldest nerve fiber population, unmyelinated fibers take part in many evolutionarily significant functions, including pain transduction, autonomic functions, and plasticity following injury. The unmyelinated fibers generally are used by the body to sense significantly strong stimuli such as those producing pain and temperature sensations. The myelinated fibers sense weaker stimuli, with the largest myelinated nerves responding to the weakest stimuli, such as a light touch, muscle sensation, and hair movement.

Previous researchers have attempted physiological isolation and study of these different nerve fibers, achieving varying degrees of success. Methods used include manipulation of nerve temperature, application of chemicals or pressure to the nerve, and versions of electrophysiological anodal or cathodal block of conduction along the nerve fiber.

Traditional electrophysiological stimulation conditions place anode and cathode electrodes along a nerve and a direct current is passed between the electrodes. The positive potential generated by the cathode stimulates the nerve fibers of appropriate diameter (large fibers first by weaker stimulations, then progressively smaller axons are also recruited with increasingly stronger stimulations) and action potentials travel in both directions along the axon. The anode in this case is often placed distal to the desired direction of action potential conduction because when the action potential generated by the cathode reaches the negative potential region adjacent to the anode it may be blocked by the negative potential. However, the signal propagates unimpeded along the nerve fiber in the opposite direction.

The anodal electrophysiological block works on the principle of electrically hyperpolarizing the region of axons under an anode electrode to such an extent that the invading electrical potentials cannot depolarize the local membrane to the response threshold thereby causing conduction failure. Just as the difference in axoplasmic resistances of the different fiber types allows generation of action potentials in large myelinated fibers in response to weaker stimuli than smaller diameter fibers, it also makes the larger fibers more susceptible to the hyperpolarizing effects of an anode. Evidence concerning the relationship of blocking threshold (defined as that level of the polarization or blocking signal required to block conduction in a given fiber type) to fiber size shows that it tends to be more hyperbolic than linear. Such a relationship strongly favors the ability to block conduction in the larger fibers while still allowing conduction in smaller ones.

Electrophysiological techniques have been employed with varying degrees of success, but there have been consistent problems associated with their application that have limited their usefulness. Such problems include damage to the nerve by the polarization or as a necessity of the preparation, long polarization periods which disallow rapid repetition of block, inability to reproduce effective separation in larger nerves, necessity of exposing a large area of nerve, and generation of undesired synchronous and asynchronous activity by the polarization itself. The application of blocking current must be precisely controlled to avoid nerve damage and destruction. Too intense a current can kill the nerve and thus the area of application of current to the nerve must be such that the current density does not reach destructive levels.

BRIEF SUMMARY OF THE INVENTION

An object of the present invention is to provide a reproducible and reversible electrophysiological method for selectively controlling propagation of naturally evoked activity of myelinated nerve fibers.

Another object is to pass direct current into the nerve in a manner to avoid inducing action potentials in any fibers while blocking existing action potentials in large diameter fibers.

A further object is to provide a technique that avoids nerve damage and other problems associated with previous electrical nerve response blocking methods.

Yet another object is to provide special electrodes and electronic components for producing a differential current density required by the present technique.

The present invention constitutes a technique for blocking nerve signal transmission that uses polarizing electrodes of different sizes and differential current densities to successfully create a differential block of larger myelinated nerve fibers without blocking the relatively smaller unmyelinated C-fibers. A key feature of this technique is the utilization of a relatively small anode in comparison to the cathode so that the current density at the anode is high and relatively low at the cathode. As a result, it is possible to selectively block nerve activity by applying current to these electrodes without activating the nerve fibers in either direction. Thus the current applied to these electrodes blocks nerve transmission, but does not produce excitation of the nerve. This novel blocking method and apparatus are versatile and can be utilized to block naturally occurring nerve activity or activity induced by another set of electrodes.

In the preferred embodiment, a narrow anode electrode is placed on the nerve proximate to the destination of the action potentials, and a wide circumferential trough cathode electrode is used distally from the destination point. The preferred electrodes are comprised of a conductive foil or coating such as silver with a silver/silver chloride coating shaped in the form of a nerve-receiving trough. The electrodes preferably are spaced apart from 2.0 millimeters to about 4.0 millimeters as a direct function of nerve size. A current is ramped to a final intensity of between about 0.020 milliamperes to about one milliampere preferably and is sent through the electrodes and the nerve for approximately one millisecond to up to a few minutes, with 200 milliseconds to 1 second being preferred.

The present invention is further illustrated by the experimental work that is described herein.

DETAILED DESCRIPTION OF THE INVENTION

Figure 1:
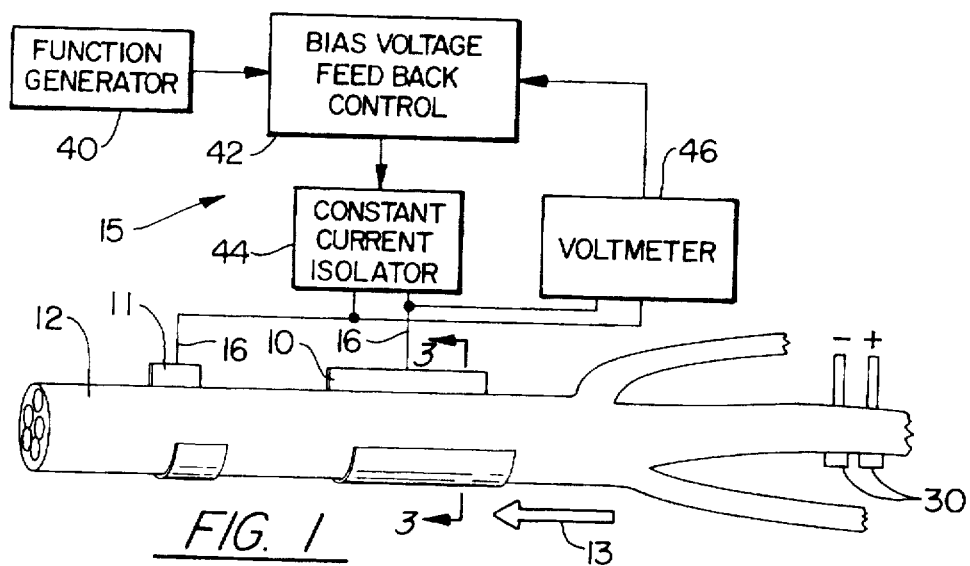
FIG. 1 is a simplified schematic drawing of the connection of blocking electrodes to a nerve.

With initial reference to FIG. 1, a pair of electrodes 10 and 11 are attached to a nerve 12 through which a response to stimulation travels in a direction indicated by arrow 13. The nerve 12 contains myelinated and unmyelinated nerve fibers 6. Specifically, a smaller electrode 11 is placed proximate to the destination of nerve activity, while a larger electrode 10 is placed distally from the destination point. The two polarizing electrodes 10 and 11 are spaced 2.0 to 4.0 millimeters apart. The smaller electrode 11 acts as the conduction. blocking anode while the larger electrode 10 serves as the cathode, as a result of connection to the corresponding polarity output terminals of a DC signal generator 15. The larger cathode electrode 10 distributes the current over a greater area of contact with the nerve 12, thereby reducing the current density and the magnitude of the effect that the current has on the nerve as compared with the smaller anode electrode 11. It also reduces the spatial requirements in reference to many other DC polarization methods and does not appear to damage the nerve as reported for other methods (see Thorén P., Shepherd J. T., and Donald D. E., "Anodal Block of Medullated Cardiopulmonary Vagal Afferents in Cats," *J. Appl. Physiol.: Respirat. Environ. Exercise Physiol.* 42:461–465, 1977; and Guz A. and Trenchard D. W., "The Role of Non-Myelinated Vagal Afferent Fibers From the Lungs in the Genesis of Tachypnea in the Rabbit," *J. Physiol.*, London, 213:345–371, 1971). The density of current was vital to separately controlling the conduction in different types nerve fiber types, i.e. a selective nerve block, but also poses the greatest threat to the health of the nerve 12.

Figures 2, 3:
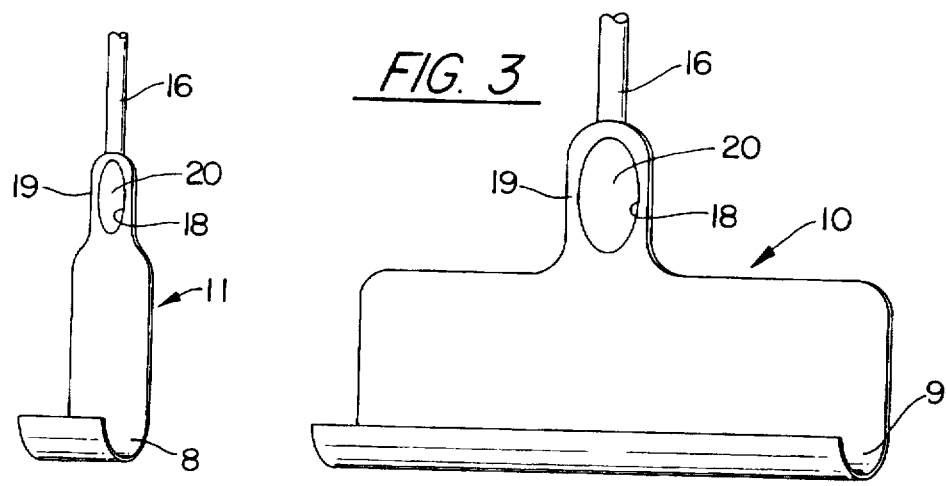
FIG. 2 illustrates the preferred anode electrode.
FIG. 3 illustrates the preferred cathode electrode.

As shown in FIGS. 2 and 3, the polarizing electrodes 10 and 11 are trough shaped for the application of differential polarization (or blocking) current densities to the nerve 12. The terms "polarization current" and "blocking current" are used interchangeably herein and refer to the current signal applied to electrodes 10 and 11 by the signal generator 15. The preferred anode electrode 11 has a 0.5 to 1.0 millimeter long (measured as length of contact with nerve along the long axis of the nerve) trough 8 which contacts the nerve 12 and the cathode electrode has a 6.0 millimeters long trough 9, so as to be at least six times greater in size than the anode trough 8 for minimum nerve damage and optimum blocking performance.

Figure 4:
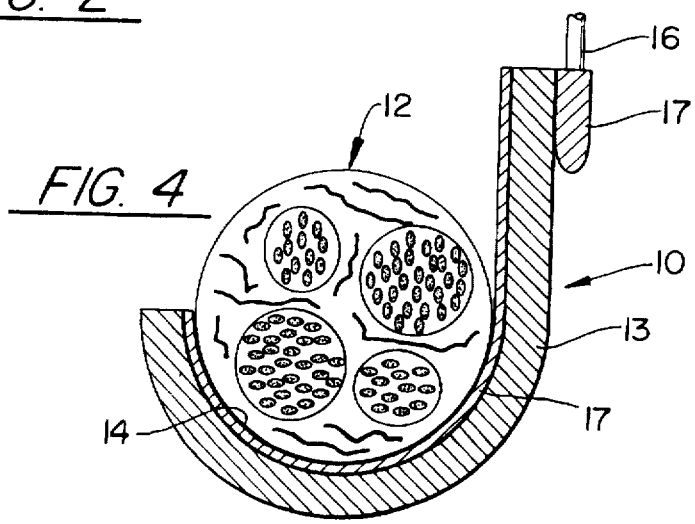
FIG. 4 is an enlarged cross sectional view taken along line 3—3 in FIG. 1.

With additional reference to FIG. 4, for laboratory use the polarizing electrodes 10 and 11 comprise a base 13 of 0.05 millimeters thick silver foil with a surface having a coating 17 of silver chloride. Flat foil is first cut into the desired shape with an oval aperture in a connection tab 19. The foil base 13 is lightly sanded to remove oxidation and any foreign substances. Then, a silver wire 16 is attached to the foil by solder 20 at the aperture 18 with care being taken to use only minute amounts of solder 20 and to solder only a small edge of the foil to maintain the vital flexibility of the electrode. Neither solder nor solder flux (if used) is allowed to contact the surface of the foil that subsequently will be in contact with the nerve 12. The flat foil base 13 next is chlorinated with a sodium chloride (NaCl) and silver hydroxide (AgOH) solution to produce the silver chloride (AgCl) coating 17 and then is bend carefully around a mold, such as an appropriate diameter metal rod.

The illustrated trough electrodes 10 and 11 are used for relatively small nerves, which require contact with the electrodes over only part of the circumference of the nerve as shown in FIG. 4. Larger nerve fibers may require full circumferential contact with the electrodes. However, bending these foil electrodes 10 and 11 fully around larger nerve fibers may cause the AgCl coating 17 to crack and flake. To circumvent this problem, electrodes for larger nerves can be made in two parts each similar to the electrodes shown in FIGS. 2 and 3, but with a smaller arc so that the two parts encase the full circumference of the nerve when combined. Each part is bent into a half-tube shape and then coated with AgCl.

Alternatively when the polarizing electrodes 10 and 11 are to be implanted into an animal, the a base 13 of each electrode may be fabricated from a silicone tube having a concave surface coated with an electrically conductive material.

The signal generator 15 shown in FIG. 1 produces the polarizing direct current waveform for the electrodes. This blocking current ranges between about 0.02 milliamperes to about one milliampere, which is sent through the electrodes 10 and 11 for a period from approximately one millisecond to up to a ten minutes, with a 100 millisecond to 1 second period being preferred. The DC signal generator 15 includes a function generator 40 that produces the waveform for the blocking polarization. For example the function generator may be either a trapezoid generator (such as made by Fredrick Haer Corporation) for plateau polarizations, or a function generator (such as a Tektronics model FG-501A) to produce a triangular waveform. The output of the function generator 40 is coupled to a differential amplifier 42 (such as Tektronics model AM-502) which acts as a DC-offset bias voltage feedback control to maintain the interelectrode potential at zero volts between applications of blocking polarizations. The output of the differential amplifier 42 is applied to a conventional constant-current linear stimulus isolator 44 (such a models manufactured World Precision Instruments), which pass the polarizing current to the electrodes 10 and 11 via conductors 16. The outputs of the constant-current linear stimulus isolator 44 are connected to inputs voltage monitor 46 that has an output coupled to the differential amplifier to control the interelectrode potential between applications of blocking polarizations.

Experimental Results

The novel blocking electrodes 10 and 11 were evaluated experimentally on the caudal cutaneous sural (CCS) nerve from male rats that had been dissected free from the sciatic trunk or on the sciatic nerve just proximal to the popliteal fossa. The blocking electrodes 10 and 11 were applied to the nerve 12 as shown in FIG. 1 and a pair of stimulation electrodes 30 also were applied to the dissected nerve about 20 millimeters from the blocking cathode 10. The signal generator 15 and the stimulating electrodes 30 were driven by a Grass S88 stimulator. Activity was recorded from the intact dorsal root and centrally cut root filaments as described by Johnson R. D. and Munson J. B. in "Regenerating Sprouts of Axotomized Cat Muscle Afferents Express Characteristic Firing Patterns to Mechanical Stimulation", *J. Neurophysiology*, 66:2155–2158, 1991. In some cases, the recordings were made from fascicles teased from the sciatic nerve at the hip. Records of single and averaged events were stored using an on-line digital signal averaging program running on a personal computer. Both analog and digital oscilloscopes were employed for real-time monitoring of the electrical events occurring in the in situ preparation.

Conduction velocity (CV) determinations were made by dividing the conduction distance (measured post-mortem between the proximal-most stimulating electrode and the closest recording electrode) by the conduction latency (time from onset of stimulus artifact to onset of response). The conduction velocity demarcations used in the figures correspond to the general conduction velocity ranges for the A$\delta$ and C-fibers in rat peripheral nerve. Specific conduction velocity ranges for afferent fiber groups in the rat were difficult to ascertain from the literature as the recording preparations and the controlled variables differed across experiments. For purposes of this invention any fiber conducting between 2.0 and 12.0 m/sec is in the A$\delta$ range, and below 2.0 m/sec is considered to be a C-fiber. It should be noted that DC polarization current alters conduction velocity.

The data suggested that the stimulation distance was great enough to remove the distal stimulus from effects of the blocking current, if any were present. In some tests, the polarity of the blocking electrodes 10 and 11 was reversed placing the cathode remote from the stimulation point. A certain level of cathodal blocking was possible, but unlike preferred anodal block, complete separation of nerve type blocking was not achieved. The cathodal block was far less reliable, and more difficult to maintain and adjust.

More effective and reliable block was produced with the more narrow anodes, while activation was decreased and eventually removed with the wider cathodes. After testing a battery of combinations within separate single experiments, it was determined that for blocking current applied to the sural nerve, a 6.0 millimeters distally placed cathode in combination with a proximally placed narrow anode (from a less than 0.5 millimeters diameter silver wire to a 1.0 millimeters foil strip) provided the best results. Thus a minimum cathode to anode size differential of six to one is preferred.

The effect of altering the distance between the polarizing electrodes during anodal block was noted. If the electrodes 10 and 11 were too close (less than 1.0 millimeter) the effectiveness of the block decreased, probably due to the polarizing current short circuiting across the fluid or epineurium. If the electrodes 10 and 11 were moved too far apart (distance varies with nerve size and preparation), the separate electrodes apparently began to act in a monopolar fashion (see potential measurements during bipolar distance changes in Hopp F. A., Zuperku E. J., Coon R. L., Kampine J. P.; "Effect of Anodal Blockade of Myelinated Fibers on Vagal C-fiber Afferents", *Am. J. Physiol.* 239:R454–R462, 1980). This caused a decrease in blocking threshold that was accompanied by an increase in activity generated directly by the polarization block. The spacing which offered the most functional and reproducible results was between 2.0 and 3.0 millimeters.

Effects Of Polarization Peak Magnitude

Figure 5:
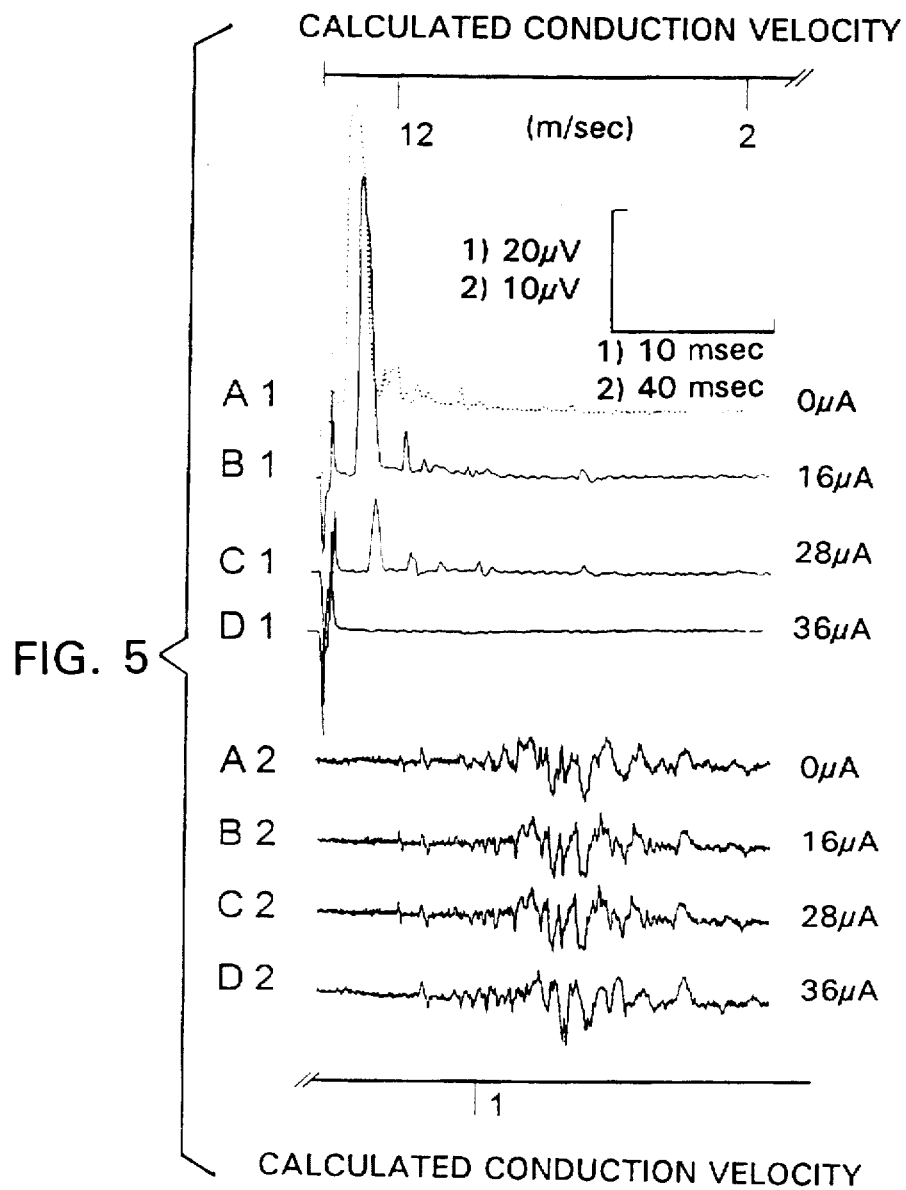
FIGS. 5A and 5B graphically show the effects of polarization peak magnitude on the conduction of caudal cutaneous sural (CCS) nerve A- and C-fibers.

The distal electrical stimuli at electrodes 30 were timed to generate a compound action potential such that the A-fiber component would arrive at the blocking site at the peak of the polarization signal waveform ramp. This provided the greatest probability that conduction in the large fibers would be blocked. FIGS. 5A and 5B show the effects of polarization current peak magnitude on the conduction of CCS nerve A- and C-fibers resulting from a varied polarization peak with the ramp times and distal stimulus strength and delay held constant. The traces depict averaged nerve response to C-fiber strength stimulation of the distal CCS nerve with increasing strength of blocking polarization current. Trace A is a control response of C-fiber strength CCS stimulation with no block present. The peak magnitudes of blocking current were: B-16 µA; C-20 µA; D-28 µA; and E-36 µA. The distal stimulation was timed such that the A-fiber CAP (Compound Action Potential) encountered the blocking site at the peak of polarization current. The onset time of the polarization was 400 msec. The traces in FIG. 5A are strictly the responses of the A-fibers while the set in FIG. 5B shows the C-fiber responses of the respective traces above. The horizontal and vertical scales are 10 msec and 20 mV for FIG. 5A; and 40 msec and 10 mV for FIG. 5B. Calculated conduction velocity is indicated on the lines beneath each set of traces.

It is clear from the experiments that there was an increase in block effectiveness as the peak of the polarization current was increased, and that the C-fibers continued to conduct.

Effects Of Distal Stimulus Timing

Figure 6:
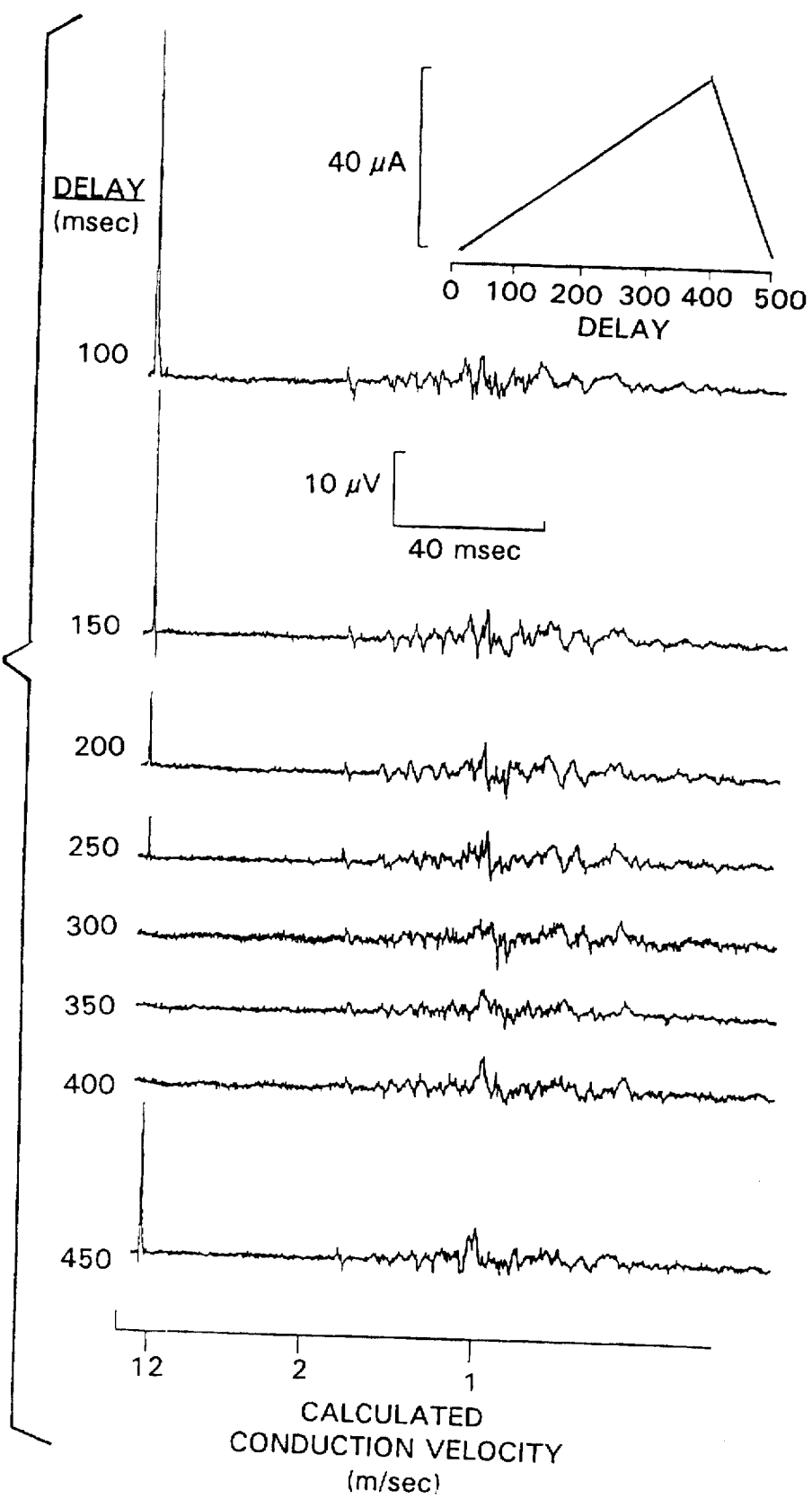
FIG. 6 are tracings which show effects of distal electrical stimulus timing relative to blocking polarization on the effectiveness of the block.

FIG. 6 presents tracings showing effects of the distal electrical stimulus timing relative to blocking polarization on the effectiveness of the block. Traces are of the averaged nerve response while the delay between polarization onset and C-fiber strength distal CCS stimulation was varied. The applied blocking waveform is represented in the inset with its own scales. The delay points in reference to the polarization onset are indicated both under the waveform (inset) and to the left of the corresponding response traces. Stimulus artifacts have been removed for clarity.

It is clear that as the distal stimulus at electrodes 30 was timed such that the A-fiber CAP reaches the blocking electrodes with the polarization current at increased strengths, more of the A-fiber population was blocked. The C-fiber population, however, conducted through the block, even though at the shorter delays it is these fibers whose activity encountered a more polarized blocking site than did their myelinated counterparts as they have slower conduction. Conduction distance from stimulating electrodes 30 to blocking anode 10 in these tests was 20–25 millimeters.

The results of this study indicate that as the stimulus was timed to have the A-fiber CAP arrive at the block site at increasingly more polarized times, the block became more effective. It should be noted that there was a blocking window created by the fact that block was effective for a period before and after the actual ramp peak. This window varied with the slope of the ramp and how far the polarization peak exceeded blocking threshold. It also should be noted that the C-fibers continued to conduct even though the timing was such that they often encountered the polarized region of the nerve when the polarization was at or near its peak.

Effects Of Polarization Ramp Slope

Figure 7:
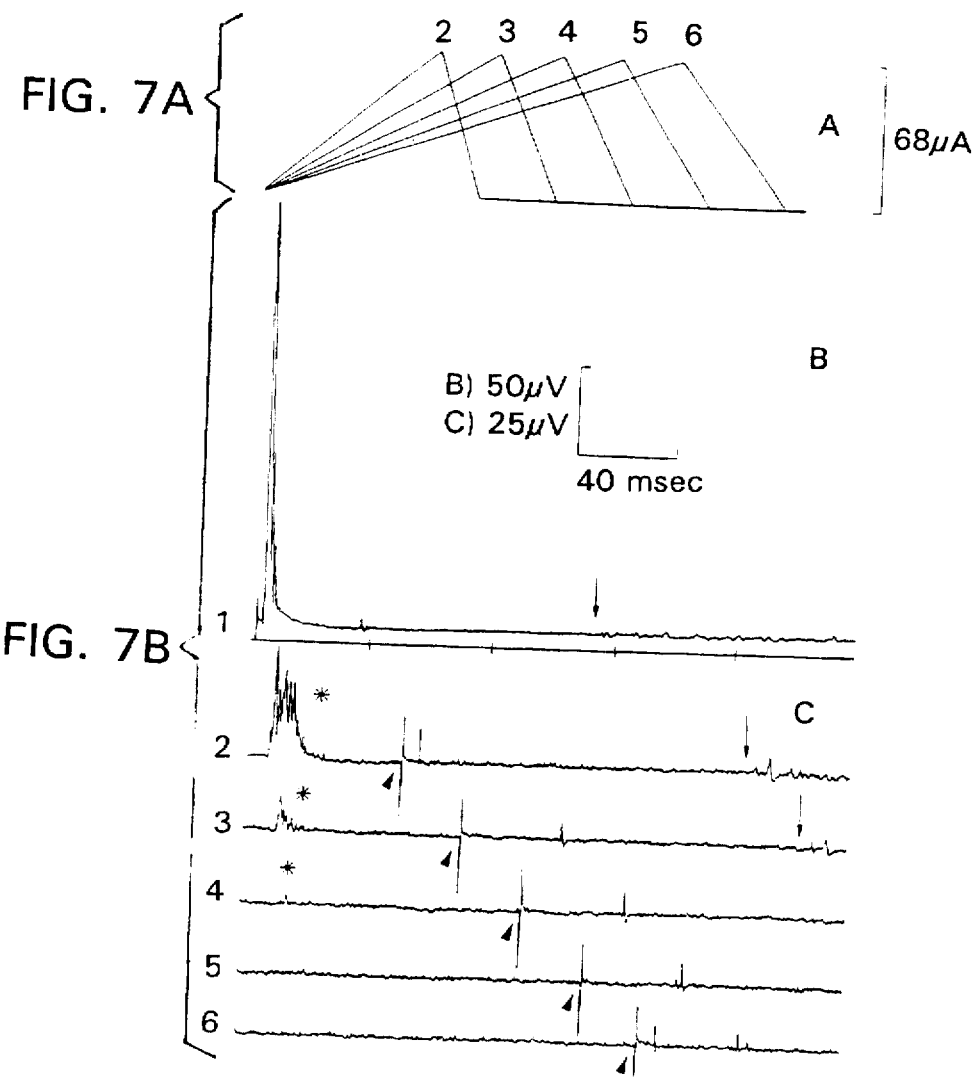
FIG. 7A depicts blocking current waveforms of different slopes.
FIG. 7B shows traces the blocking effectiveness and activation of nerve fibers for each current waveform.
Figure 8:
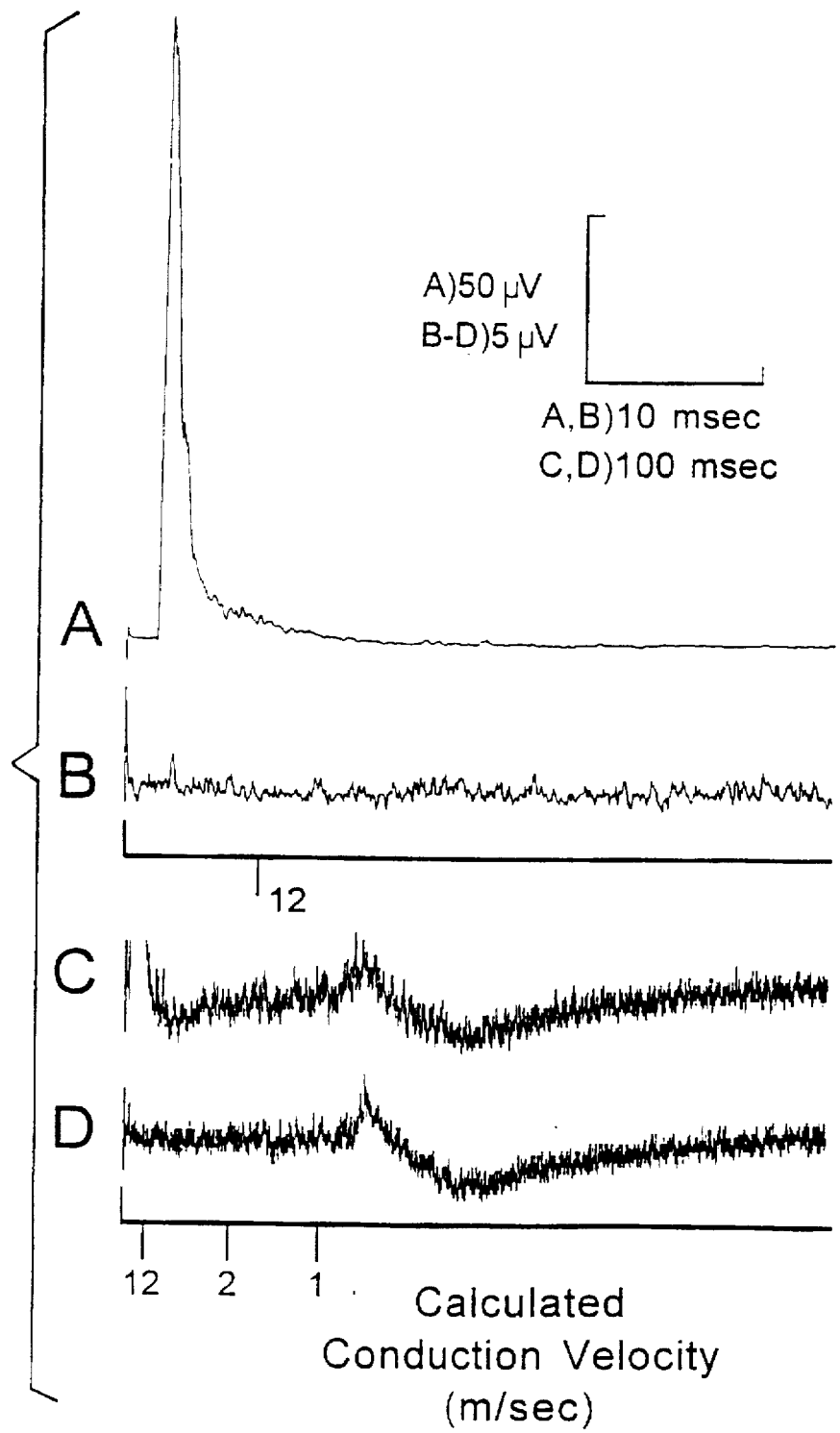
FIG. 8 presents tracings of the averaged nerve response to C-fiber strength distal stimulation of the CCS nerve with blocking electrodes placed on the sciatic nerve.

Using a polarization current peak that was shown to allow only small fiber conduction, the slopes of the polarization current waveforms were varied as illustrated in FIG. 7A. Throughout the course of the study it was clear that there was a threshold slope under which the polarization onset had to remain in order to avoid the polarization itself causing activation of the nerve. For the differential current density polarization block to be effective and avoid fiber activation in the larger sciatic nerve, a longer polarization slope was required (850 msec to a polarization peak of 200 µA; see FIG. 8). Although the onset time had to be increased for the larger sciatic nerve, the block was clearly effective. Typical activation induced by each correspondingly numbered waveform slope is shown in traces 2–4 of FIG. 7B with a vertical scale maximum of 25 microvolts. Trace 1, having a 50 microvolt maximum vertical scale, represents the control in which no blocking current was applied to electrodes 10 and 11. The time scale for all the traces in FIGS. 7A and 7B are the same. Note that the activation was removed as the slope was decreased.

Distal stimulus artifacts are pointed to by triangles in FIG. 7B, and their timing corresponds directly to the matching polarization ramps in A. Regardless of onset slope, all polarization ramps were capable of accurately blocking A-fiber conduction and allowing C-fiber conduction. A single Aβ (traces 2 and 6) and a single Aδ (traces 3–6) fiber were also allowed to conduct. The C-fiber responses were identical for traces 1–6, but were outside of the plotted window in traces 4–6. The full C-fiber response can be seen in trace 1 and the beginning of the response seen at the end of traces 2 and 3 (arrows).

The grade of the offset slope was far more flexible, but depended somewhat on the magnitude of the polarization peak. In many cases its duration could be shortened as far as 10 milliseconds without generating the "break" excitation of a square wave.

Effects Of a Polarization Plateau

In order to test whether it would be possible to increase the blocking window and reliably block high frequency stimuli, a "trapezoidal" polarization signal was applied to the nerve via the special electrodes. This polarization exhibited the same ability to block the large fibers as did the triangular polarization. It also allowed small fiber conduction at high rates of repetition.

Figure 9:
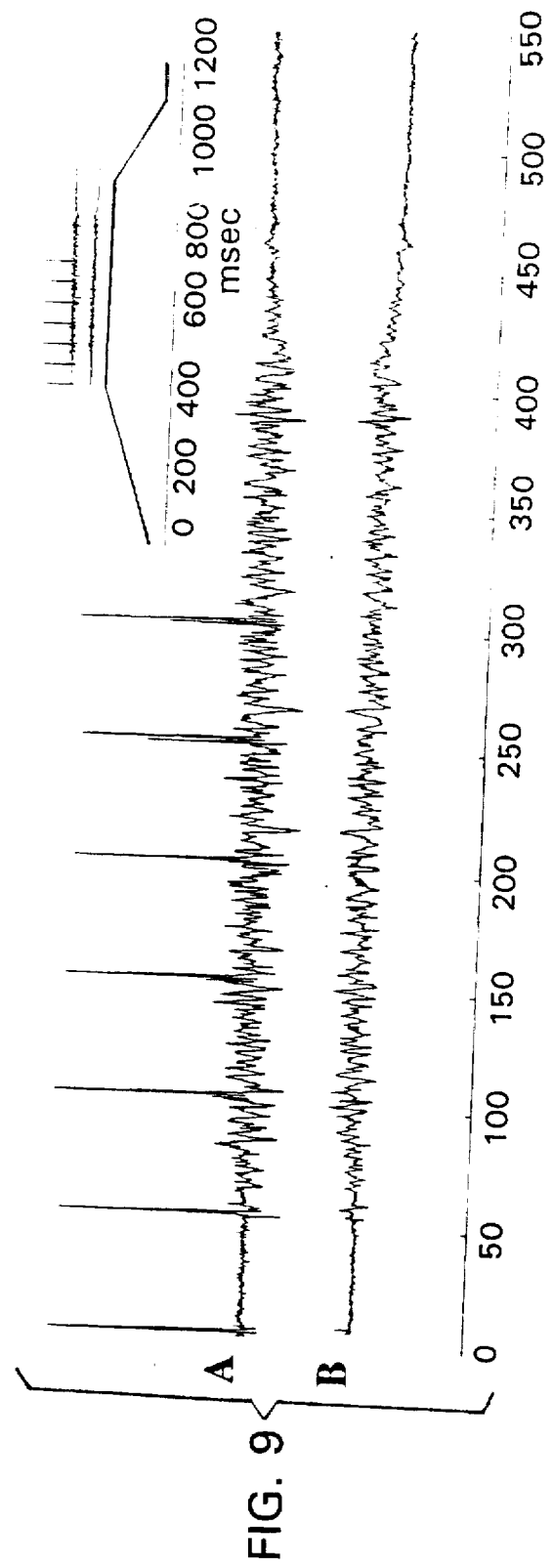
FIG. 9 shows tracings depicting block efficacy during extended polarization and application of a train of stimuli.

The tracing of FIG. 9 show block efficacy during extended trapezoidal polarization and application of a train of stimuli. Each trace represents the averaged nerve response to a C-fiber strength stimulus train (20 Hz, 300 msec duration) to the distal CCS without and with blocking polarization in traces A and B respectively. The parameters of the trapezoidal polarization waveform were an onset ramp of 400 msec, plateau of 500 msec, offset ramp of 200 msec, and a magnitude of 52 mA for the full duration of the plateau shown in the inset. Recording window in B begins with the blocking plateau with stimulus artifacts subtracted out for figure clarity. Note that if a high frequency C-fiber strength activation of the distal nerve is applied during the polarization plateau, only the C-fibers conduct through the block.

Effects Of Block on Natural Stimulation

Figure 10:
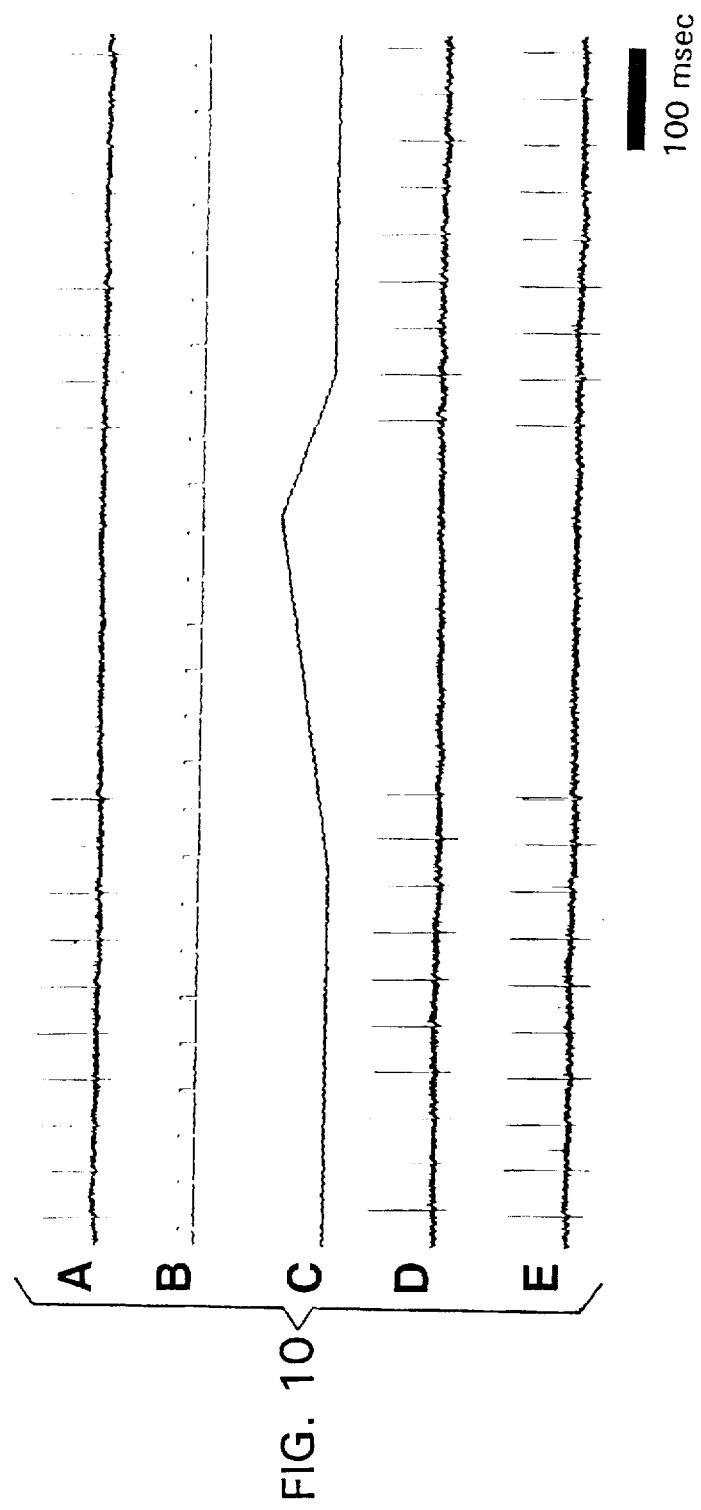
FIGS. 10 are tracings showing effects of polarization block on natural stimulation of CCS nerve territory.

FIG. 10 shows that the blocking polarization generated reliable fiber type separation for natural stimuli as well as electrical. In FIG. 10 traces are of unaveraged single unit A-fiber responses to natural stimulation. Blocking electrodes were on the proximal CCS. Records were taken from a filament teased from dorsal root. The tibial and common peroneal nerves were crushed. Natural stimulation (low amplitude tapping) to the receptive field of a rapidly adapting mechanoreceptor was applied using a Chubbock mechanostimulator driven by 20 Hz square-wave pulses from a Grass S11 stimulator (shown in B). During the repetitive application of the mechanical stimulus, the polarization block was presented (represented in C). A, B, and C are all recordings of the same event on separate channels (A is the nerve response, B is the mechanical stimulus trigger, C is the blocking polarization). The neural response records in D and E are from subsequent applications of the blocking polarization during the continued mechanical stimulation. The peak of the polarization was 100 µA. Stimuli were not applied with the intention of recruiting C-fiber activity.

Figure 11:
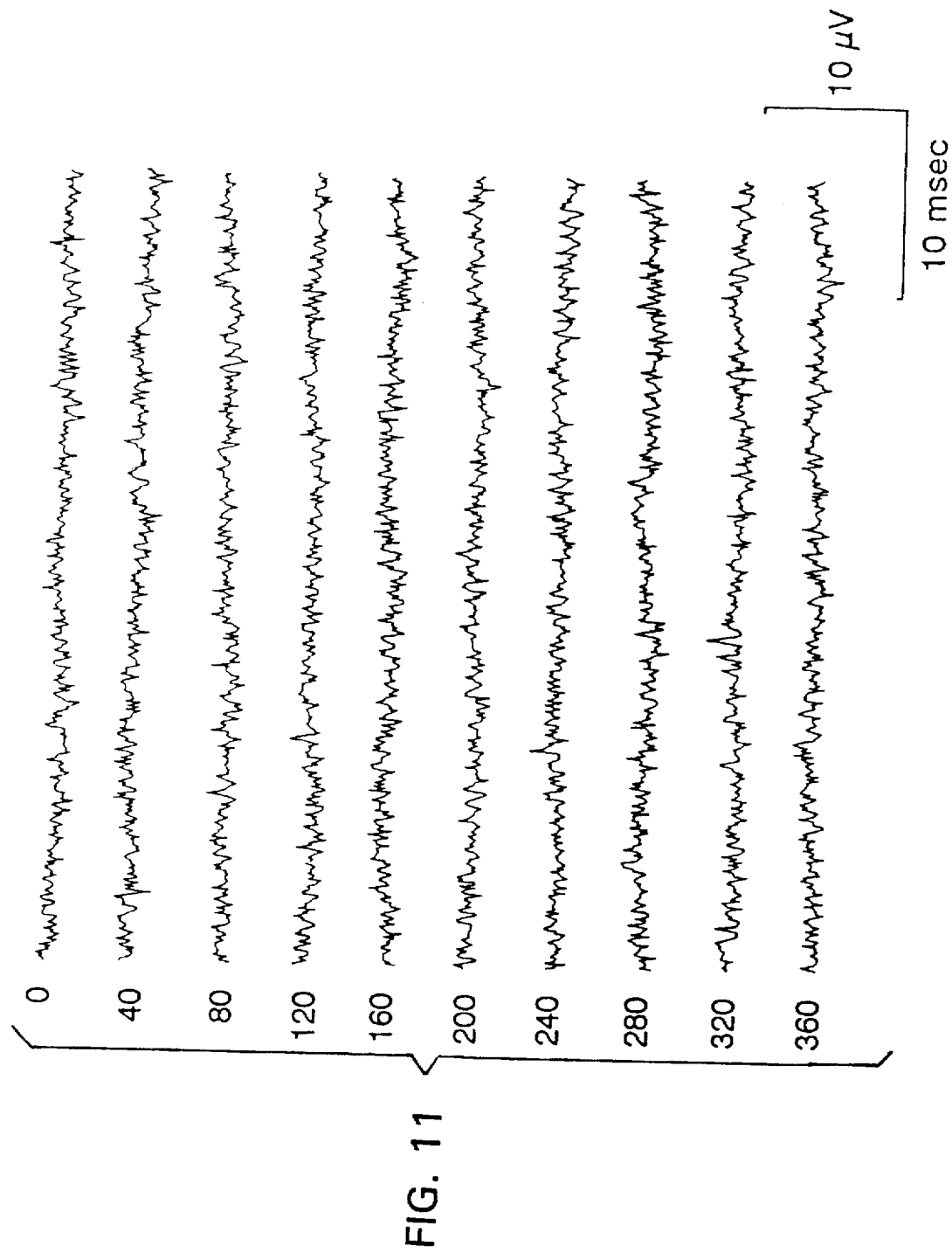
FIG. 11 illustrates traces that show a 400 millisecond recording from the site of distal nerve stimulation during a period of blocking polarization and show that the blocking signal does not produce any activity.

FIG. 11 presents traces showing a 400 millisecond recording from the site of distal nerve stimulation during a period of blocking polarization. It shows that the polarization that blocks the large fibers does not itself produce any activity.

The results of the above experimental work indicated that reproducible and reversible selective conduction using the electrodes of the present invention could be achieved utilizing anodal polarization. The effectiveness of the conduction separation relied on a number of factors. These included the electrode geometry, the amplitude and onset slope of the polarizing current, the timing of the stimulus to the polarization, and the nerve involved. Proper balance of these factors allowed consistent block of conduction in the A-fiber population without blocking C-fiber conduction.

Figure 12:
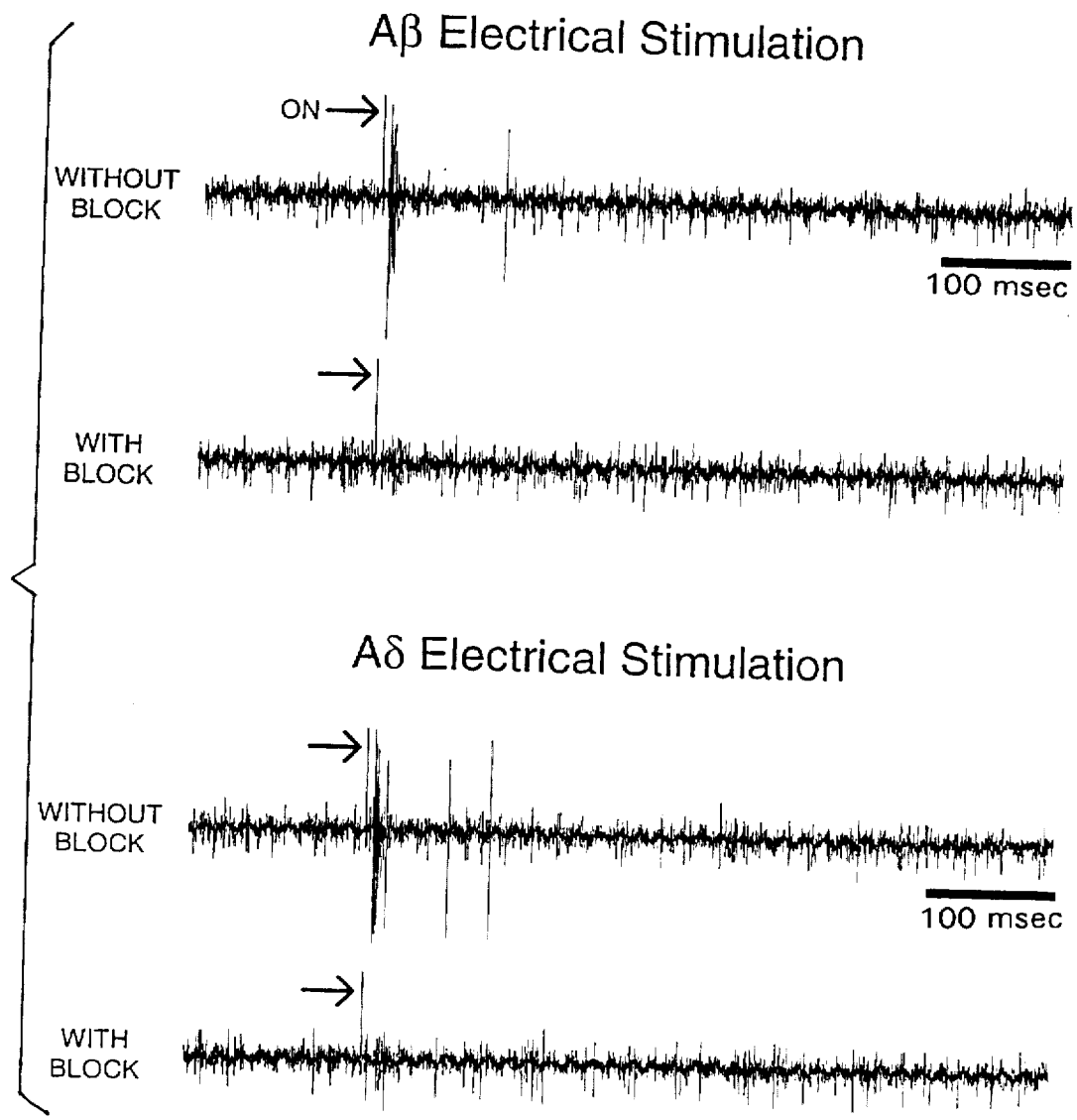
FIGS. 12 and 13 are graphs the represent experiments conducted on a single unit isolated in a nucleus gracilis.
Figure 13:
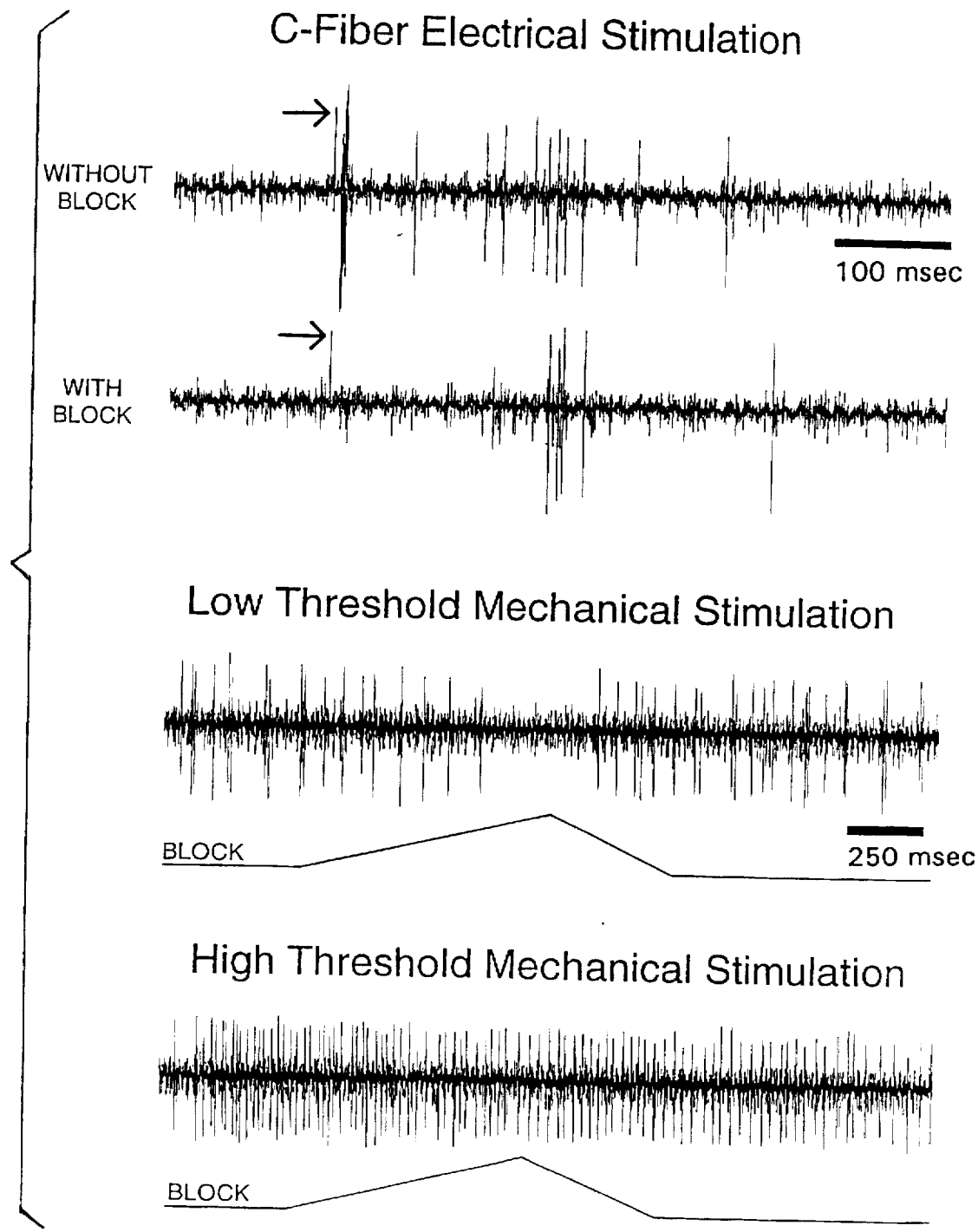

FIGS. 12 and 13 record experimental results of a single unit isolated in the isolated in a nucleus gracilis. Each trace is the response of the unit to a single electrical pulse stimuli (presented to the peripheral nerve beginning at a point designated by the arrow), or to a natural stimulus which was present throughout the timecourse shown in the traces. The single electrical stimulus pulses were timed to the peak of the polarization ramp. The strength of each electrical stimulus pulse is indicated by the title above each pair of traces.

Figure 14:
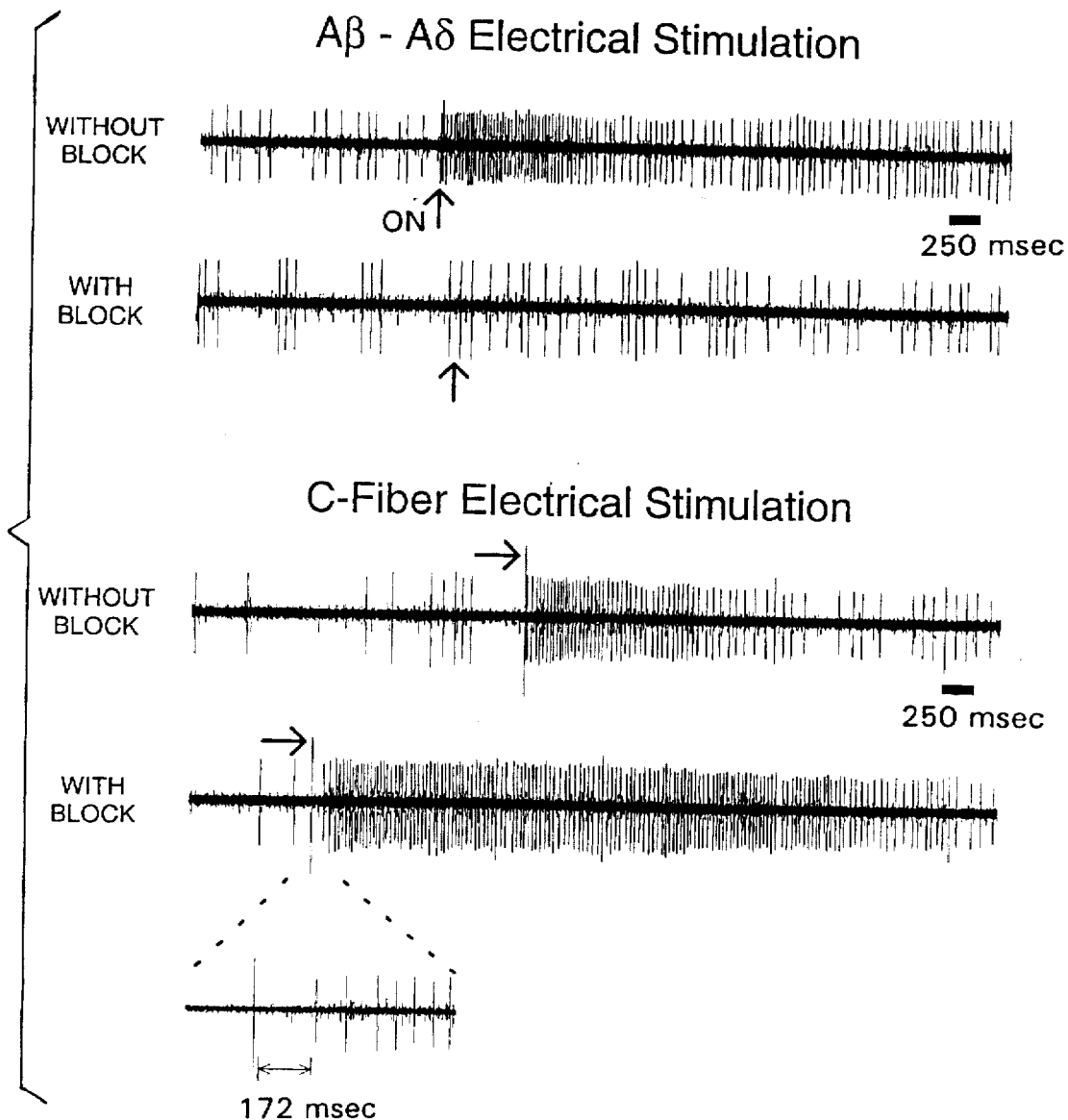
FIG. 14 graphically depicts results of experiments conducted on a single unit isolated in a nucleus reticularis gigantocellularis.

FIG. 14 graphically depicts results of experiments conducted on a single unit isolated in a nucleus reticularis gigantocellularis. The AδAβ traces are the response of the unit to a 50 msec train of Aδ-strength electrical stimulus pulses presented to the peripheral nerve. Timing of the stimulus is indicated by the arrows. Activity in the "with block" trace is equivalent to background activity. The C-fiber traces are the responses of the unit to single C-fiber strength electrical stimulus pulses. Note the immediate response of the unit in the "without block" trace. One also can observe from the "with block" trace (see also the inset) that the immediate response is eliminated, with the first onset of the response occurring at a latency highly consistent with the expected conduction delay of a strictly C-fiber input. Also note the increased response duration and frequency due to a strictly C-fiber input.

Conclusion

As the results of the experimental work clearly indicate, anodal DC polarization is capable of producing separate control of Aδ- and/or C-fibers from the larger myelinated fibers. As mentioned earlier, the mechanism of action under the anode is most likely hyperpolarization to a level that disallows invading action potentials to depolarize the local membrane to suprathreshold levels. In contrast, the classical view of conduction block via accommodation (cathodal block) is that a slowly increased depolarization, as used here and elsewhere, will cause the h-gates of the voltage activated sodium channels to close before the channel pore itself opens in response to voltage change. Polarity reversal of the bipolar anodal blocking setup, placing the cathode remote to the stimulation origin, produced a differential block that was less accurate and more sensitive to ramp slopes and tissue-electrode interface differences.

Polarization via the special electrodes does not itself cause any activation of nerve fibers when applied properly. This is different from many other attempts at nerve control.

The present invention has many advantages over other DC polarization separation techniques. It requires only short, low intensity polarization ramps and allows very controlled current application. The controlled current application allows shorter polarization ramps and reduces the probability of producing undesired activity. This reduces net current injection and allows safer polarization of the nerve. This invention allows for the safe extension of polarization times to allow for separation during multiple stimulations during a DC plateau and is capable of allowing selective propagation of myelinated fiber activity generated either electrically or by natural stimulation. These properties, in addition to the modest and flexible spatial requirements, makes the invention useful in a wide range of applications.

We claim:

1. An apparatus for selectively blocking activity of a nerve in an animal by application of electric current, said apparatus comprising:

an anode having a first surface with an electrically conductive first area for contacting the nerve;

an cathode having a second surface with an electrically conductive second area for contacting the nerve, wherein the second area is at least six times greater in size than the first area so that density of current conducted between the cathode and the nerve is much less than the density of current conducted between the anode and the nerve;

a signal generator which produces a direct current blocking polarization signal at positive and negative output terminals; and conductors which connect the anode to the positive output terminal and the cathode to the negative output terminal.

2. The apparatus as recited in claim 1 wherein the anode has a curved trough portion for receiving the nerve and the first area is formed on an inside curved surface of the curved trough portion.

3. The apparatus as recited in claim 1 wherein the cathode has a curved trough portion for receiving the nerve and the second area is formed on an inside curved surface of the curved trough portion.

4. The apparatus as recited in claim 1 wherein the anode has a first curved trough portion for receiving the nerve and the first area is formed on an inside curved surface of the first curved trough portion; and the cathode has a second curved trough portion for receiving the nerve and the second area is formed on an inside curved surface of the second curved trough portion, wherein the second curved trough portion is at least six times longer than the first curved trough portion.

5. The apparatus as recited in claim 4 wherein the first curved trough portion is substantially 0.5 to 1.0 millimeters long, and the second curved trough portion is substantially 6.0 millimeters long.

6. The apparatus as recited in claim 1 wherein the anode and the cathode are spaced apart 2.0 to 4.0 millimeters along the nerve.

7. The apparatus as recited in claim 1 wherein the signal generator produces a trapezoidal direct current blocking polarization signal.

8. The apparatus as recited in claim 1 wherein the signal generator produces a triangular direct current blocking polarization signal.

9. The apparatus as recited in claim 1 wherein the signal generator comprises a function generator having a output; a bias-voltage feedback control circuit connected to the output of the function generator; a constant-current linear stimulus isolator receives an output signal from the feedback control circuit and produces the direct current blocking polarization signal; and a voltage monitor which senses a potential between the anode and the cathode and produces a signal indicative of that potential which is applied to the bias-voltage feedback control circuit.

10. An apparatus for selectively blocking activity in specific types of fibers within a nerve in an animal by application of electric current, said apparatus comprising:

an anode having base with a first surface which has a first area for contacting the nerve, the first area is coated with an electrically conductive material;

an cathode having base with a second surface which has a second area for contacting the nerve, the second area is coated with an electrically conductive material, and wherein the second area is at least six times greater in size than the first area so that density of current conducted between the cathode and the nerve is much less than the density of current conducted between the anode and the nerve;

a signal generator which produces a direct current blocking polarization signal at positive and negative output terminals; and conductors which connect the anode to the positive output terminal and the cathode to the negative output terminal.

11. The apparatus as recited in claim 10 wherein the base of the anode and the base of the cathode are both formed of a material which conducts electricity.

12. The apparatus as recited in claim 10 wherein the base of the anode and the base of the cathode are both formed of silver.

13. The apparatus as recited in claim 10 wherein the first area of the anode and the second area of the cathode are both coated with silver chloride.

14. The apparatus as recited in claim 10 wherein the base of the anode and the base of the cathode are both formed of silicone.

15. The apparatus as recited in claim 10 wherein the anode has a first curved trough portion for receiving the nerve and the first area is formed on an inside curved surface of the first curved trough portion; and the cathode has a second curved trough portion for receiving the nerve and the second area is formed on an inside curved surface of the second curved trough portion, wherein the second curved trough portion is at least six times longer than the first curved trough portion.

16. A method, for selectively blocking activity in specific types of fibers within a nerve of an animal, said method comprising steps of:

attaching an anode to the nerve thereby forming a first area of nerve contact;

attaching an cathode to the nerve thereby forming a second area of nerve contact, wherein the second area is at least six times greater in size than the first area; and applying a direct current blocking polarization signal between the anode and the cathode, whereby density of current conducted between the cathode and the nerve is at least one-sixth the density of current conducted between the anode and the nerve, because of difference in sizes of the first and second areas.

17. The method for selectively blocking activity of a nerve as recited in claim 16 wherein the direct current blocking polarization signal is intermittently applied between the anode and the cathode; and further comprising maintaining the interelectrode potential at zero volts between intermittent applications of the blocking polarization signal.

18. The method for selectively blocking activity of a nerve as recited in claim 16 further comprising coating the first and second areas with a conductive material, prior to attaching the anode and the cathode to the nerve.

19. The method for selectively blocking activity of a nerve as recited in claim 16 wherein the step of applying applies a trapezoidal direct current blocking polarization signal between the anode and the cathode.

20. The method for selectively blocking activity of a nerve as recited in claim 16 wherein the step of applying a direct current blocking polarization signal applies current substantially between 0.020 milliamperes and one milliampere.

21. The method for selectively blocking activity of a nerve in an animal as recited in claim 16 wherein the step of applying a direct current blocking polarization signal applies current for a period of between one millisecond and ten minutes.

22. The method for selectively blocking activity of a nerve in an animal as recited in claim 16 wherein the step of applying a direct current blocking polarization signal applies current for a period of substantially 100 milliseconds.

* * * * *

UNITED STATES PATENT AND TRADEMARK OFFICE
CERTIFICATE OF CORRECTION

PATENT NO. : 5,755,750
DATED : May 26, 1998
INVENTOR(S) : Petruska et al.

It is certified that error appears in the above-identified patent and that said Letters Patent is hereby corrected as shown below:

<u>Column 1,</u>
Line 8, please insert the following:

-- STATEMENT REGARDING FEDERALLY
SPONSORED RESEARCH OR DEVELOPMENT

This invention was made with government support under contract no. 1-P01NS27511, awarded by the National Institute of Health, and the United States Government has certain rights in this invention. --

Signed and Sealed this

Eleventh Day of February, 2003

JAMES E. ROGAN
*Director of the United States Patent and Trademark Office*